(12) United States Patent
Kaneko et al.

(10) Patent No.: US 9,089,264 B2
(45) Date of Patent: Jul. 28, 2015

(54) MEDICAL COIL, METHOD OF MANUFACTURING THE SAME, AND MEDICAL INSTRUMENT

(71) Applicant: OLYMPUS MEDICAL SYSTEMS CORP., Tokyo (JP)

(72) Inventors: Yoshihisa Kaneko, Hachiojo (JP); Yutaka Yanuma, Hachiojo (JP)

(73) Assignee: OLYMPUS CORPORATION, Tokyo (JP)

( * ) Notice: Subject to any disclaimer, the term of this patent is extended or adjusted under 35 U.S.C. 154(b) by 49 days.

(21) Appl. No.: 13/736,360

(22) Filed: Jan. 8, 2013

(65) Prior Publication Data

US 2013/0190560 A1 Jul. 25, 2013

Related U.S. Application Data

(63) Continuation of application No. PCT/JP2012/068731, filed on Jul. 24, 2012.

(30) Foreign Application Priority Data

Sep. 12, 2011 (JP) ................................ 2011-198265

(51) Int. Cl.
*A61B 17/00* (2006.01)
*A61M 25/00* (2006.01)
(Continued)

(52) U.S. Cl.
CPC .............. *A61B 1/018* (2013.01); *A61B 1/0011* (2013.01); *A61B 17/221* (2013.01);
(Continued)

(58) Field of Classification Search
CPC ............... A61B 19/22; A61B 19/2203; A61B 2019/2242; A61B 1/018
USPC .................. 606/1; 29/557; 174/108; 604/526
See application file for complete search history.

(56) References Cited

U.S. PATENT DOCUMENTS 4,271,845 A 6/1981 Chikashige et al.
7,905,877 B1 * 3/2011 Jimenez et al. ............... 604/525
(Continued)

FOREIGN PATENT DOCUMENTS

GB 1119158 7/1968
GB 2 209 577 A 5/1989
(Continued)

OTHER PUBLICATIONS

Aug. 28, 2012 International Search Report issued in International Application No. PCT/JP2012/068731 (with translation).
Sep. 3, 2013 Extended European Search Report Issued in European Application No. 12831594.2.

*Primary Examiner* — Lynsey Crandall
*Assistant Examiner* — Sebastian X Lukjan
(74) *Attorney, Agent, or Firm* — Oliff PLC

(57) ABSTRACT

A medical coil is provided which is formed by winding an element wire, and includes a convex part provided on a first end of a width direction of the element wire, and a concave part provided on a second end of the width direction of the element wire. At least one of the convex part and the concave part has a slant face. When a compressive force is applied in an axial direction of the medical coil, the convex part and the concave part adjacent to each other are configured to approach each other. A segment which connects a top part of the convex part which protrudes the most and a deepest part of the concave part which is deepest forms an angle so as not to be parallel to an axis of the medical coil.

6 Claims, 12 Drawing Sheets

(51) Int. Cl.
  *H01B 7/18* (2006.01)
  *B23P 13/04* (2006.01)
  *A61B 1/018* (2006.01)
  *A61B 1/00* (2006.01)
  *A61B 17/221* (2006.01)
  *A61B 19/00* (2006.01)
  *A61B 17/29* (2006.01)
  *A61M 25/09* (2006.01)

(52) U.S. Cl.
  CPC ........... *A61M 25/0012* (2013.01); *A61B 19/22* (2013.01); *A61B 19/2203* (2013.01); *A61B 2017/00305* (2013.01); *A61B 2017/00526* (2013.01); *A61B 2017/2905* (2013.01); *A61B 2019/2242* (2013.01); *A61M 25/005* (2013.01); *A61M 2025/09108* (2013.01); *A61M 2025/09133* (2013.01)

(56) References Cited

U.S. PATENT DOCUMENTS

| | | | |
|---|---|---|---|
| 2007/0233043 A1* | 10/2007 | Dayton et al. | 604/526 |
| 2009/0112063 A1 | 4/2009 | Bakos et al. | |
| 2010/0298636 A1* | 11/2010 | Castro et al. | 600/104 |
| 2011/0077678 A1* | 3/2011 | Ryan et al. | 606/191 |

FOREIGN PATENT DOCUMENTS

| | | |
|---|---|---|
| JP | A-57-59519 | 4/1982 |
| JP | A-8-131550 | 5/1996 |
| JP | A-2004-261463 | 9/2004 |
| JP | A-2006-247148 | 9/2006 |
| JP | A-2006-314714 | 11/2006 |
| JP | A-2008-48850 | 3/2008 |
| WO | WO 2008/064399 A1 | 6/2008 |

* cited by examiner

MEDICAL COIL, METHOD OF MANUFACTURING THE SAME, AND MEDICAL INSTRUMENT

This application claims priority to and the benefit of Japanese Patent Application No. 2011-198265 filed on Sep. 12, 2011, and is a continuation application of PCT International Application No. PCT/JP2012/068731 filed on Jul. 24, 2012. This application incorporates the disclosures of both of the Japanese patent application and the PCT international application herein by reference.

BACKGROUND OF THE INVENTION

1. Field of the Invention

The present invention relates to a medical coil, a method of manufacturing the same, and a medical instrument.

2. Background Art

When a calculus forms in an organ such as a biliary tract or a bladder, the calculus has an adverse influence on a patient. Particularly, an enlarged calculus inflicts tremendously large pain on a patient. Thus, treatment is conducted in such a way that a treatment tool (a medical instrument) for an endoscope, which is designed to crush the calculus, is introduced into a body cavity of the patient through a channel for the treatment tool of the endoscope, and captures, crushes, and discharges the calculus from the body or captures and removes the calculus from the body in the captured state.

As such a treatment tool for the endoscope, a treatment tool disclosed in Japanese Unexamined Patent Application, First Publication No. 2006-314714 is known. In the treatment tool, a basket made of a metal element wire is installed on a distal end of a manipulation wire inserted through a sheath having flexibility. The treatment tool is configured to house the basket in the sheath along with the manipulation wire. An operator crushes the calculus using the treatment tool as follows. The operator manipulates a manipulation part connected to a proximal end of the sheath, and moves the manipulation wire forward or backward, thereby capturing the calculus in the basket. The operator pulls the manipulation wire toward the manipulation part, and thereby the basket is strained. As a result, the calculus is pressed and crushed.

In the above-mentioned treatment tool for the endoscope, both flexibility for facilitating the insertion into the body cavity and compressive resistance (resistance to axial compression) for reliably transmitting a force of traction of the manipulation wire for crushing the calculus to the basket of the tip of the manipulation wire are required for the insertion part inserted into the body cavity. Typically, a coil sheath in which the metal element wire is closely wound is frequently used as a configuration having the above-mentioned two characteristics in a relatively balanced way.

SUMMARY OF THE INVENTION

According to a first aspect of the present invention, a medical coil is formed by winding an element wire, and includes a convex part provided on a first end of a width direction of the element wire, and a concave part provided on a second end of the width direction of the element wire. At least one of the convex part and the concave part has a slant face. When a compressive force is applied in an axial direction of the medical coil, the convex part and the concave part adjacent to each other are configured to approach each other. A segment which connects a top part of the convex part which protrudes the most and a deepest part of the concave part which is the deepest forms an angle so as not to be parallel to an axis of the medical coil.

According to a second aspect of the present invention, a method of manufacturing a medical coil includes positioning a pressing surface of a die so as to form a predetermined angle with respect to the axis of the medical coil to be manufactured in the first aspect, and reeling out the element wire relative to the die so that a lateral surface of a thickness direction of the element wire comes into contact with the pressing surface to wind the element wire.

According to a third aspect of the present invention, a medical instrument includes an insertion part which is longitudinal, and at least a part of the insertion part is configured to include the medical coil according to the first aspect.

In the medical instrument, the insertion part may include a first region configured to include a first medical coil and a second region configured to include a second medical coil. The first region and the second region may be different in curvature radius of a curved shape when a compressive force is applied in an axial direction.

BEST MODE FOR CARRYING OUT THE INVENTION

First Embodiment

A first embodiment of the present invention will be described with reference to FIGS. 1 to 8B. In the present embodiment, a medical coil and a method of manufacturing the medical coil will be described by way of an example.

Figure 1:
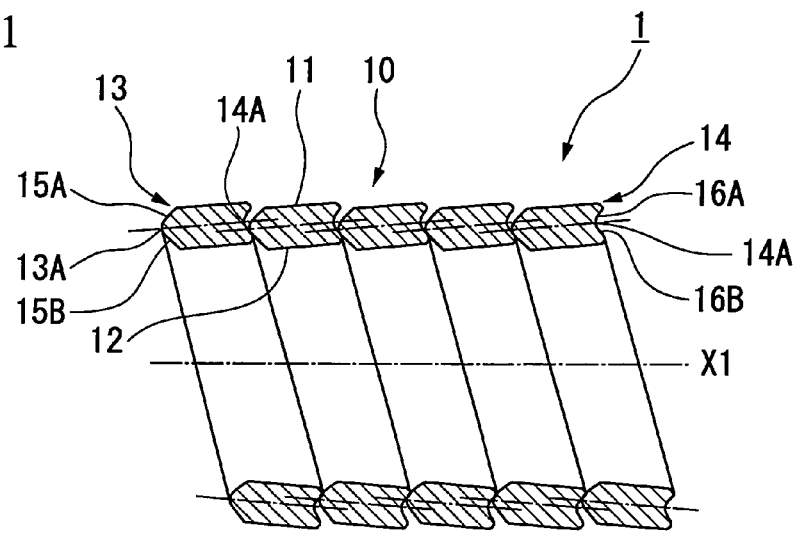
FIG. 1 is a cross-sectional view taken in an axial direction of a medical coil according to a first embodiment of the present invention.

FIG. 1 is a cross-sectional view taken in an axial direction of the medical coil 1 according to the present embodiment. The medical coil 1 is formed by closely helically winding an element wire 10 having a predetermined rigidity so as to form a plurality of loops around an axis X1. The plurality of loops are disposed on approximately the same axis, and are generally arranged in a widthwise direction of the element wire 10.

The element wire 10 has constant rigidity. As a material of the element wire 10, metal such as stainless steel or hard resin may be used. The "constant rigidity" refers to such rigidity that a shape or a cross-sectional shape (to be described below) of the formed loop is not significantly changed when the medical coil 1 is compressed in the axial direction.

The element wire 10 has a predetermined width and thickness. The element wire 10 has a basic shape as a so-called flat wire in which thickness-directional lateral surfaces 11 and 12 of the element wire 10 are formed so as to be flat. The element wire 10 is provided with a convex part 13 at a first end thereof and a concave part 14 at a second end thereof on a cross section perpendicular to a longitudinal direction thereof. The convex part 13 and the concave part 14 have slant faces 15A and 15B, and slant faces 16A and 16B, respectively, all of which are inclined with respect to the widthwise direction of the element wire 10.

A top part 13A of the convex part 13 which protrudes the most and a deepest part 14A of the concave part 14 which is deepest have the same position (including approximately the same position) in the thickness direction of the element wire. Accordingly, a segment connecting the top part 13A and the deepest part 14A is parallel to the widthwise direction of the element wire 10. Furthermore, this segment is the same as surface directions of the lateral surfaces 11 and 12, respectively.

In the medical coil 1, the element wire 10 having the above-mentioned shape is closely wound so that the lateral surfaces 11 and 12 form outer and inner circumferential surfaces of the medical coil 1, respectively.

Figure 2:
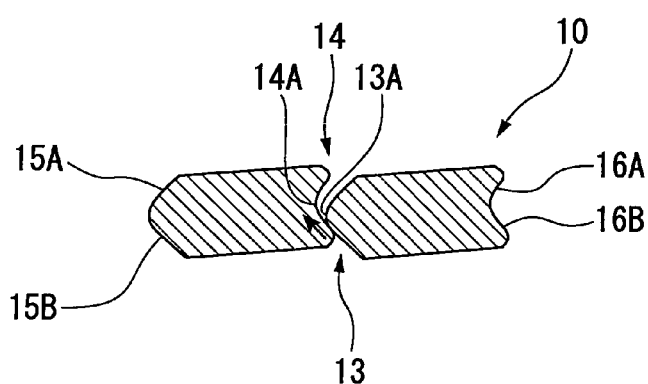
FIG. 2 is an enlarged cross-sectional view of an element wire in the medical coil according to the first embodiment of the present invention.

As shown in FIG. 2 in an enlarged form, in a natural state in which an external force is not applied, the element wire is wound in a spaced state so that the top part 13A is not in contact with the neighboring deepest part 14A of the element wire. The top part 13A is configured so as to be able to slide on a surface of the concave part 14 and to approach the deepest part 14A.

Figure 3A:
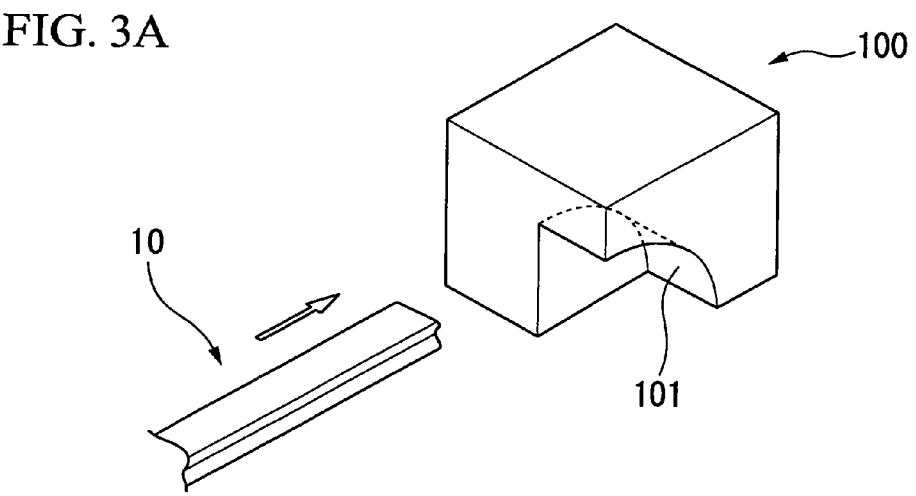
FIG. 3A is a view showing a manufacturing process of the medical coil according to the first embodiment of the present invention.
Figure 3B:
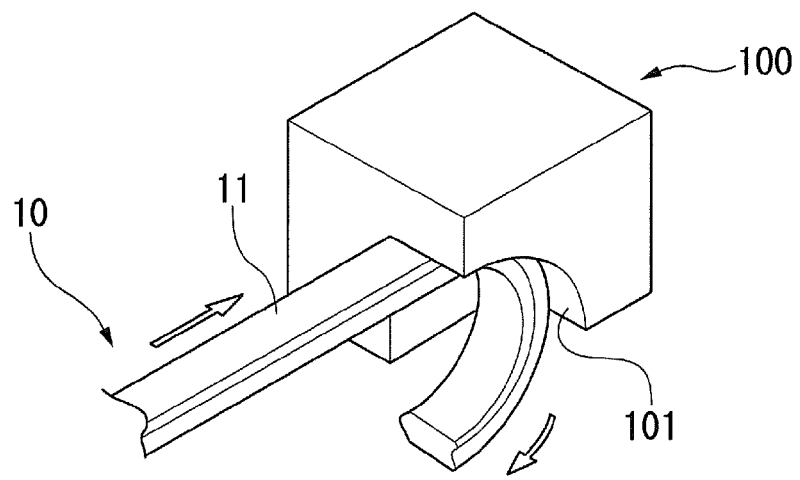
FIG. 3B is a view showing a manufacturing process of the medical coil according to the first embodiment of the present invention.
Figure 3C:
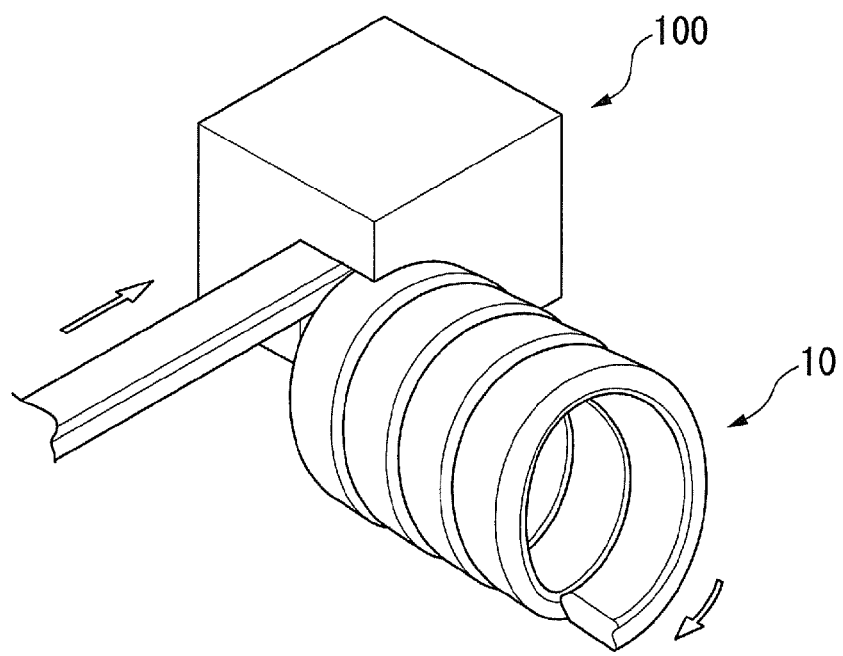
FIG. 3C is a view showing a manufacturing process of the medical coil according to the first embodiment of the present invention.

FIGS. 3A to 3C are views showing a manufacturing process of the medical coil 1. To manufacture the medical coil 1, a well-known coil winding machine is used. As shown in FIG. 3A, the coil winding machine is equipped with a die 100 having a pressing surface 101 formed in the shape of a cylinder extending in one direction. As shown in FIG. 3A, the element wire 10 moves forward and reels out in the longitudinal direction thereof, and is pressed perpendicular to an extending direction (extension direction) of the pressing surface 101. Then, as shown in FIG. 3B, the lateral surface 11 is deformed along the pressing surface 101. As shown in FIG. 3C, when the element wire 10 continues to reel out, a continuous loop is formed, and the element wire 10 is processed in a coil shape.

Figure 4:
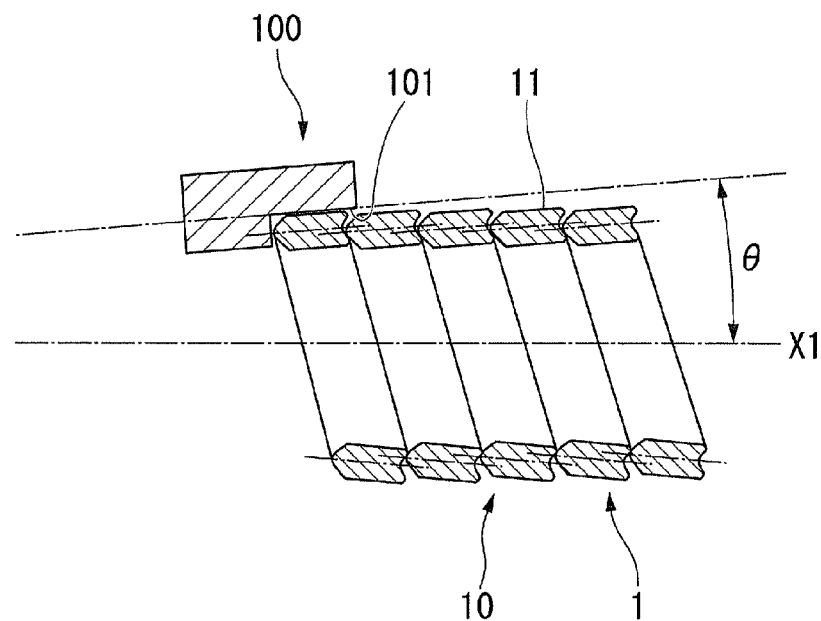
FIG. 4 is a view showing a positional relation between a medical coil and a die when manufacturing the medical coil according to the first embodiment of the present invention.

The process above is similar to a typical coil manufacturing method using the coil winding machine. However, in a method of manufacturing the medical coil according to the embodiment of the present invention, as shown in FIG. 4, the die 100 is positioned so that the extension direction of the pressing surface 101 is not parallel to the axis X1 of the manufactured medical coil 1 and is inclined by an angle θ. In this state, the process is carried out. Thereby, the element wire 10 is wound so that, in each loop of the medical coil 1, the lateral surface 11 forms the angle θ relative to the axis X1. As a result, as shown in FIG. 1, in the natural state, a state in which the top part 13A and the deepest part 14A are not in contact with each other is secured.

An operation of the above-mentioned medical coil 1 when in use will be described.

When the compressive force is applied to the medical coil 1 in the direction of the axis X1, the compressive force causes the neighboring loops of the element wire 10 to approach each other. Then, the element wires forming the neighboring loops are caused to move to a position that is most stable against the compressive force.

Figure 5:
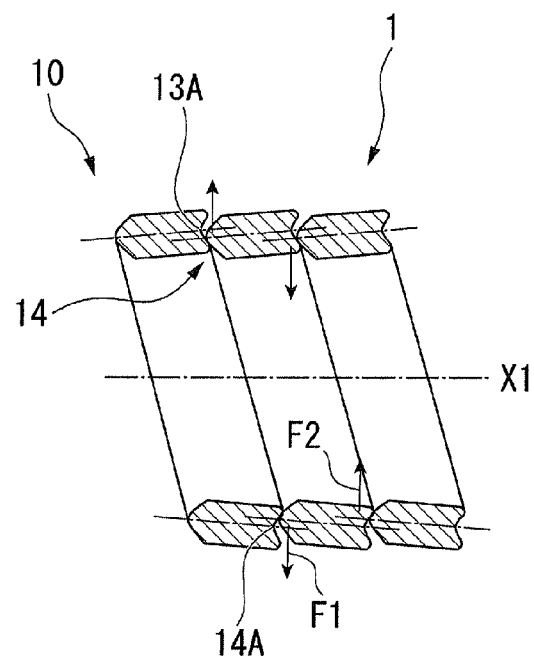
FIG. 5 is a view showing the application of force when a compressive force is applied to the medical coil according to the first embodiment of the present invention.

As described above, the top part 13A can slide on the surface of the concave part 14, and approach the deepest part 14A. As such, the top part 13A is caused to slide on the surface of the concave part 14 until it runs against the deepest part 14A. As a result, each loop is configured as shown in FIG. 5 so that force F1 is applied on the side of the convex part 13 in a direction in which a diameter of the loop is increased, and so that force F2 is applied on the side of the concave part 14 in a direction in which the diameter of the loop is reduced.

Figure 6:
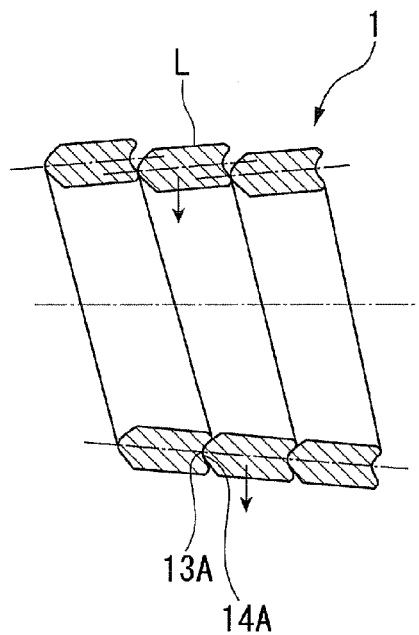
FIG. 6 is a view showing a state in which a loop is moved by the compressive force.

However, since the element wire 10 has the constant rigidity, although the compressive force is applied to the element wire 10, neither the diameter nor the cross-sectional shape of the loop is changed. Under these circumstances, when the compressive force is further increased, instead of one loop L being changed in diameter quickly and the top part 13A running against the deepest part 14A, the entire loop L moves in a radial direction of the medical coil 1 as shown in FIG. 6. The loop L has stability against the neighboring element wire in such a way that only the radial unilateral top part 13A runs against the deepest part 14A. Hereinafter, the loop L that has been displaced is referred to as a "movable loop L."

Figure 7:
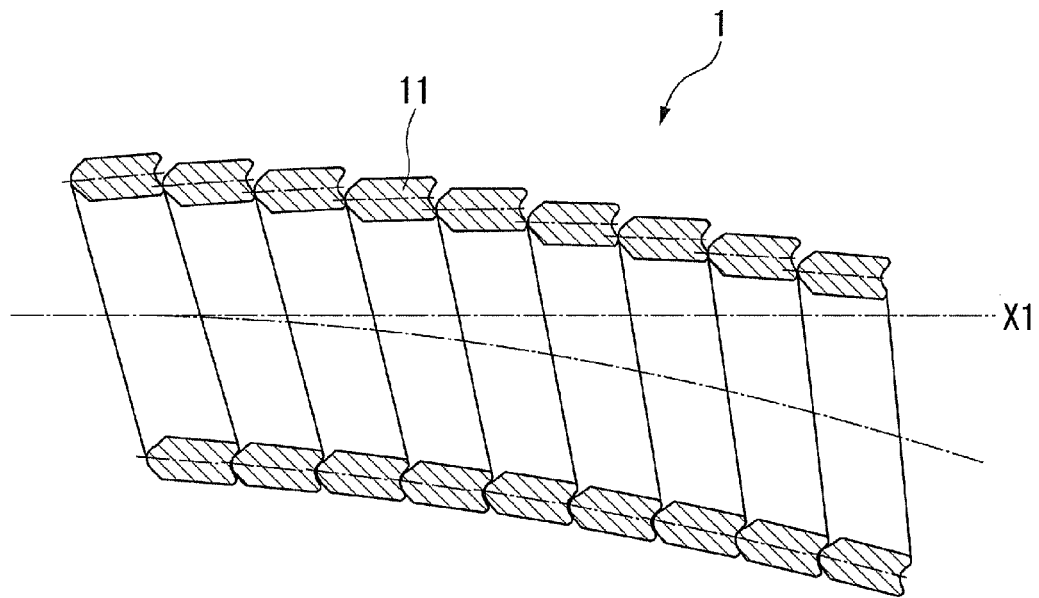
FIG. 7 is a view showing the medical coil compressed and curved in the axial direction.

When the movable loop L is displaced and stabilized in the radial direction, the movable loop L and the loop adjacent to the movable loop L on the side of the convex part 13 are locked with respect to the movable loop L. These two loops do not undergo relative displacement in the radial direction. For this reason, the loops located in front of and behind these two loops are displaced so as to be stabilized against these two loops. The loops located in front and behind are further displaced relative to the loops locked one after another. For this reason, the medical coil 1 is finally curved in one direction so as to be inclined with respect to the axis X1, as shown in FIG. 7. During compression, a curvature radius of the curvature may be adjusted within a given range by adjusting the angle θ formed between the lateral surface 11 and the axis X1 of the medical coil 1.

Figure 8A:
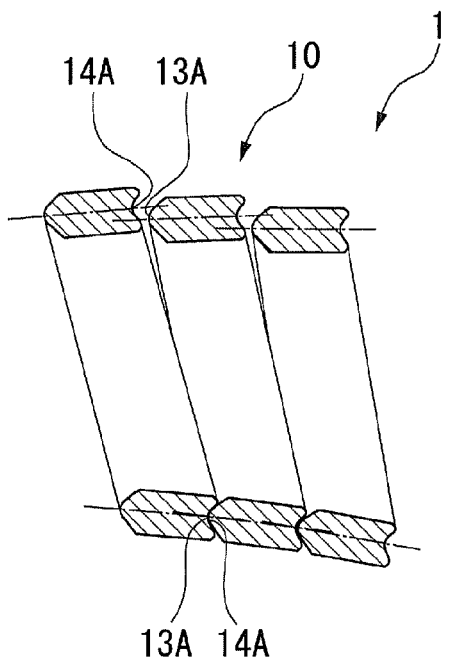
FIG. 8A is an example of a state of the medical coil before the compressive force is applied.
Figure 8B:
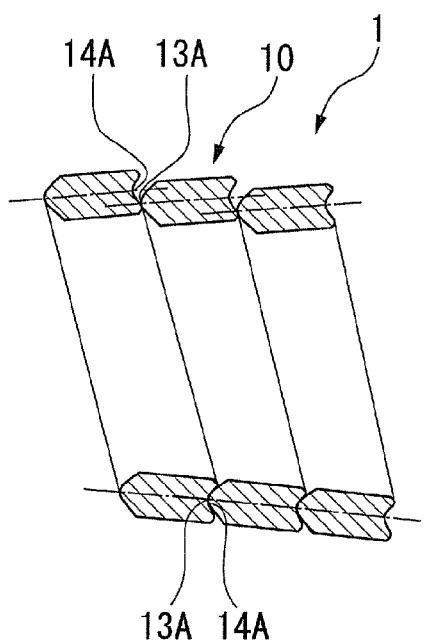
FIG. 8B is a view showing the medical coil after the compressive force is applied in the state shown in FIG. 8A.

During the compression of the medical coil 1, the direction in which the first movable loop is displaced is dependent on the state of the medical coil just before the compressive force is applied. For example, when the medical coil 1 is located inside a channel of a curved endoscope or inside a meandering lumen tissue, the medical coil 1 has already been curved in one direction. In this case, as shown in FIG. 8A, inside the curve, the top part 13A of a certain loop runs against the deepest part 14A of the neighboring loop. Since the top part 13A and the deepest part 14A may approach each other, when the compressive force is applied, the medical coil 1 is curved in the same direction as the curve before the compression, as shown in FIG. 8. That is, the medical coil 1 is curved so as to follow a shape of the channel or the lumen tissue by applying the compressive force.

As described above, according to the medical coil 1 according to the present embodiment, the element wire having the constant rigidity is wound and formed so that, in the natural state, the convex part 13 and the concave part 14 of the neighboring loops can approach each other. For this reason, the medical coil 1 does not assume the linear shape even when the compressive force is applied, and is kept in a predetermined curved state. Accordingly, by applying the medical coil to a medical instrument, an excellent effect of easily performing a procedure even under compression or of reducing a load applied to the inserted lumen tissue or endoscope can be obtained.

According to the method of manufacturing the medical coil according to the present embodiment, the above-mentioned medical coil 1 can be manufactured by simply reeling out the element wire at the first and second ends of the widthwise ends of which the convex and concave parts are formed, toward the die disposed so that the extension direction of the pressing surface thereof forms an angle relative to the axial direction of the medical coil. Accordingly, since the medical coil can be manufactured by a process substantially similar to a conventional coil manufacturing method, the medical coil according to the embodiment of the present invention can be easily manufactured.

Second Embodiment

Figure 10:
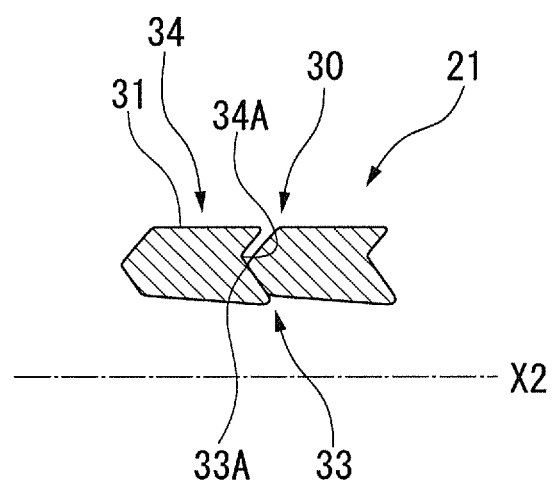
FIG. 10 is a unilateral partial cross-sectional view of the medical coil according to the second embodiment of the present invention.
Figure 11:
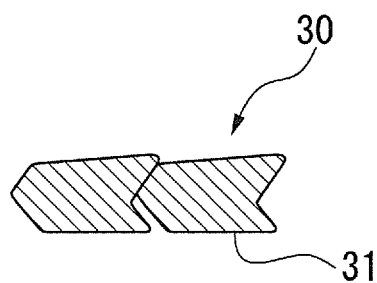
FIG. 11 is a unilateral partial cross-sectional view in a modification of the medical coil according to the second embodiment of the present invention.

A second embodiment of the present invention will be described with reference to FIGS. 9 to 11. A medical coil 21 according to the present embodiment is different from the medical coil 1 according to the first embodiment in the respect of the cross-sectional shape and the manufacturing method of the element wire.

In the following description, components common to the medical coil 1 according to the first embodiment which has been previously described are given the same reference numerals, and the repetitive description thereof will be omitted.

Figure 9:
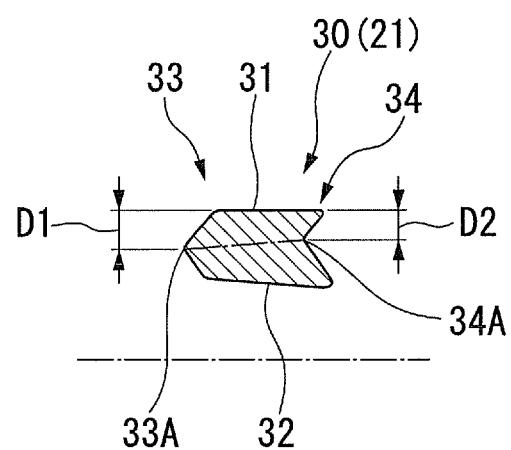
FIG. 9 is a cross-sectional view of an element wire of a medical coil according to a second embodiment of the present invention.

FIG. 9 is a view showing a cross section of an element wire 30 which is perpendicular to a longitudinal direction of the element wire 30 forming the medical coil 21. In the element wire 30, a distance D1 and a distance D2 are different from each other. The distance D1 is a thickness-directional distance between a lateral surface 31 of a first thickness-directional end and a top part 33A of a convex part 33. The distance D2 is a thickness-directional distance between the lateral surface 31 of the first thickness-directional end and a deepest part 34A of a concave part 34. The convex part 33 and the concave part 34 have slant faces 35A and 35B and slant faces 36A and 36B, respectively, all of which are inclined with respect to the widthwise direction of the element wire 30.

The medical coil 21 can be manufactured by performing a winding operation on the element wire 30 formed as described above in accordance with the related art using the above-mentioned coil winding machine equipped with the die 100. That is, the die 100 is positioned so that an extension direction of a pressing surface 101 is parallel to an axis X2 of the medical coil 21 to be manufactured. In this state, when the element wire 30 reels out perpendicular to the pressing surface 101, the medical coil 21 in which the lateral surface 31 and the axis X2 are parallel to each other is manufactured, as shown in FIG. 10 as a unilateral cross-sectional view.

In the medical coil 21, the above-mentioned distances D1 and D2 are different from each other. For this reason, in the natural state, as shown in FIG. 10, the top part 33A and the deepest part 34A in the neighboring loops are not in contact with each other. When sliding on a surface of the concave part 34, the convex part 33 can approach the deepest part 34A. Accordingly, like the medical coil according to the first embodiment, an effect of easily performing a procedure even under compression or of reducing a load applied to the inserted lumen tissue or endoscope can be obtained.

Since the medical coil can be manufactured by winding the element wire in exactly the same process as the related art, the medical coil can be more easily manufactured.

In the present embodiment, an example in which the element wire 30 is wound so that the lateral surface 31 forms an outer circumferential surface of the manufactured medical coil has been described. Instead of this, as shown in FIG. 11, the element wire 30 may be wound so that the lateral surface 31 forms an inner circumferential surface of the manufactured medical coil, and the medical coil 21A may be formed. When the medical coil 21A is manufactured in this way, using a cylindrical core rod instead of using the die, the element wire 30 may be wound with the lateral surface 31 directed toward the core rod. In this case, since the medical coil can be manufactured by a typical core rod winding process, the medical coil can be more easily manufactured.

In the present embodiment, an example in which the lateral surface 32 of a second thickness-directional end is not parallel to the lateral surface 31 is shown. However, the thickness-directional lateral surfaces may be formed so as to be parallel to each other.

Third Embodiment

A third embodiment of the present invention will be described with reference to FIGS. 12A to 15. In the present embodiment, an example of a medical instrument equipped with the medical coil according to each of the above-mentioned embodiments will be described.

Figure 12A:
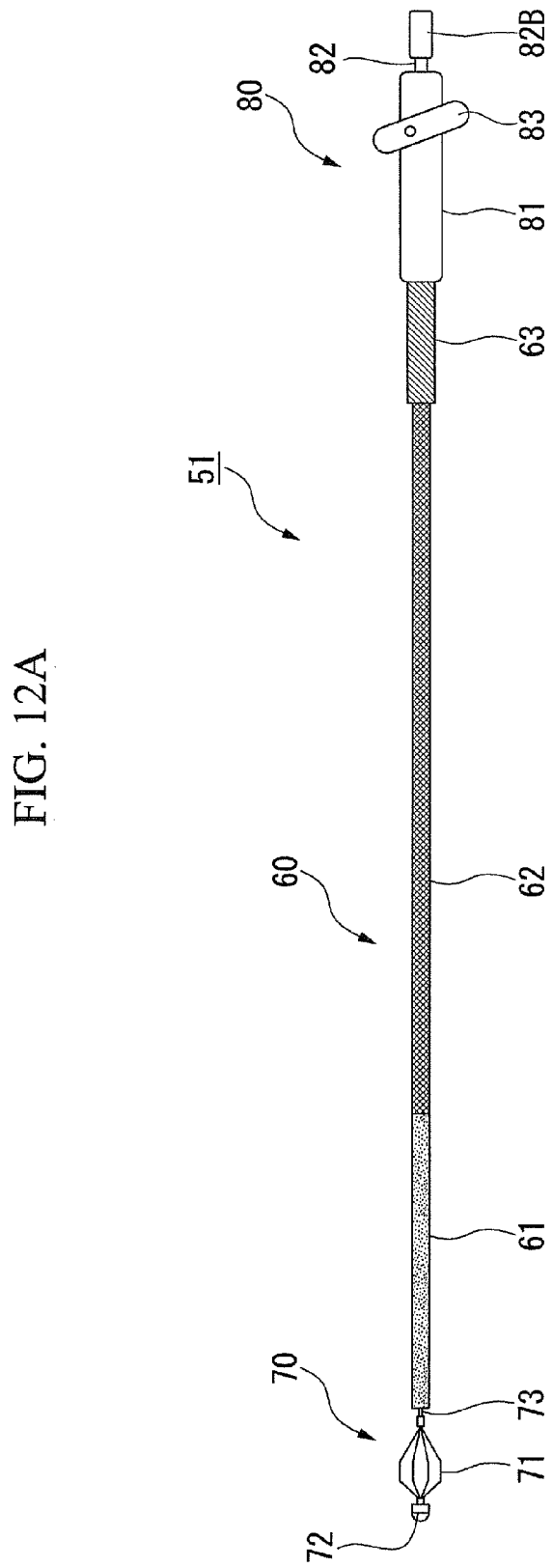
FIG. 12A is a view showing an entire configuration of a medical instrument according to a third embodiment of the present invention.
Figure 12B:
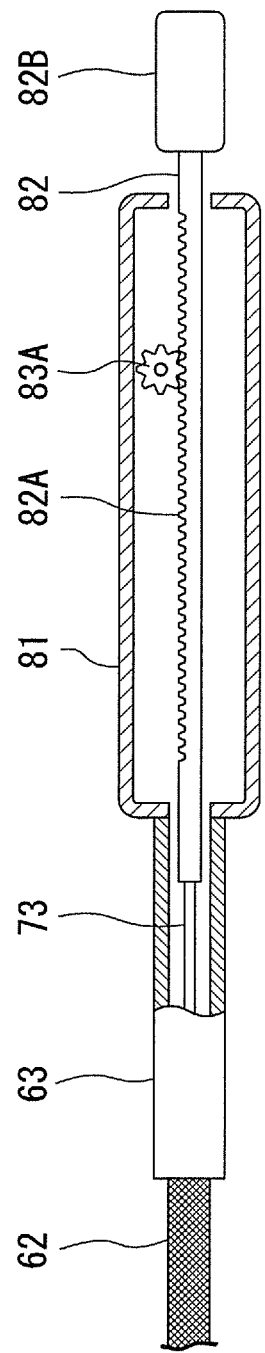
FIG. 12B is a cross-sectional view of a manipulation part of the medical instrument according to the third embodiment of the present invention.

FIG. 12A is a view showing an entire configuration of the medical instrument 51 of the present embodiment. FIG. 12B is a cross-sectional view of a manipulation part 80 of the medical instrument 51. The medical instrument 51 includes an insertion part 60, a treatment part 70, and the manipulation part 80. The insertion part 60 is formed at long length. The treatment part 70 is installed at a distal end side of the insertion part 60. The manipulation part 80 is attached at a proximal end side of the insertion part 60.

Figure 13:
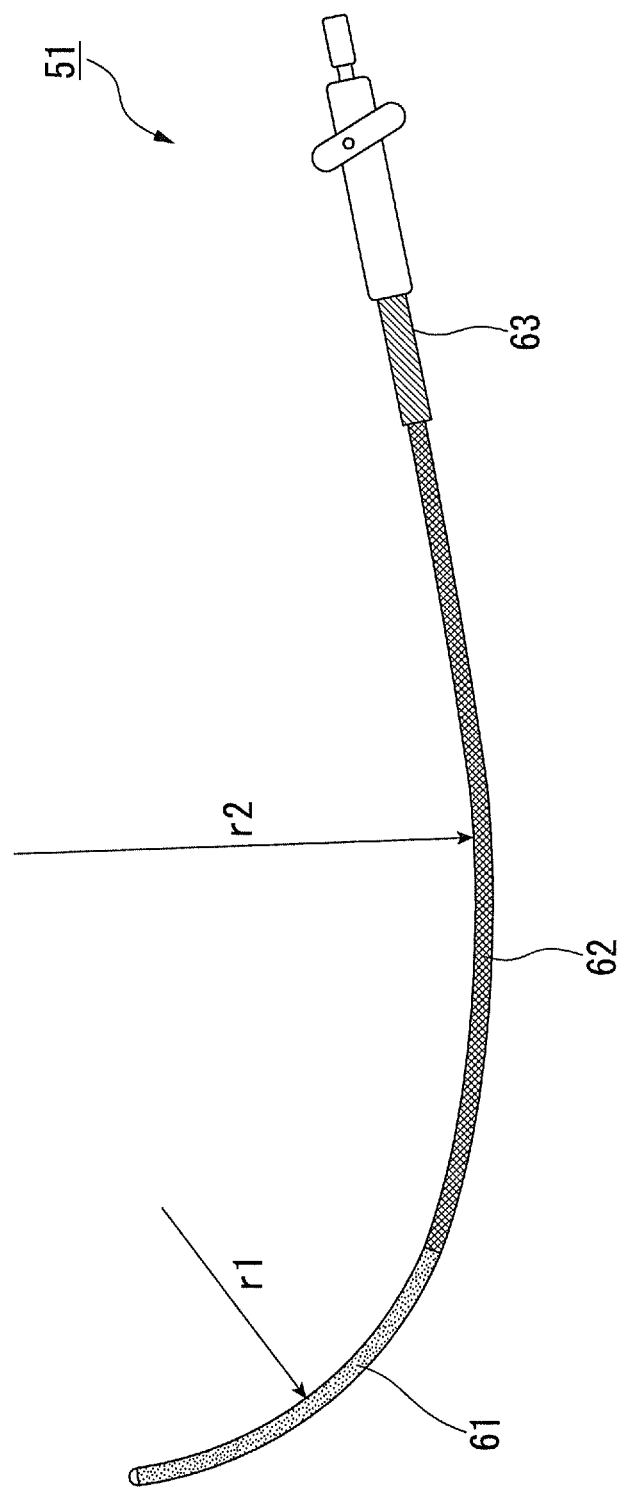
FIG. 13 is a view showing a curvature radius in an insertion part of the medical instrument according to the third embodiment of the present invention.

The insertion part 60 is formed in the shape of a long tube. The insertion part 60 includes a first region 61, a second region 62, and a third region 63. The first region 61 is located at the distal end side of the insertion part 60. The second region 62 is located at a proximal end side of the first region 61. The third region 63 is located at a proximal end side of the second region 62. Both the first region 61 and the second region 62 are made up of the medical coil according to the embodiment of the present invention. As shown in FIG. 13, when the compressive force is applied to bend the insertion part 60, a curvature radius r2 of the second region 62 is set so as to be greater than that r1 of the first region 61.

The first region 61 and the second region 62 may be integrally formed. The first region 61 and the second region 62 may be separately manufactured, and then be connected by welding. In the case in which the first and second regions are integrally formed, an angle formed by a pressing surface of a die and an axis of a coil may be changed when the first region is formed and when the second region is formed.

The third region 63 is formed of a typical coil other than the medical coil according to the embodiment of the present invention. The distal end side of the third region 63 is connected with the second region 62 by welding. The proximal end side of the third region 63 is connected with the manipulation part 80 by bonding, deposition, or press-fitting. The third region 63 is a region in which, even when a procedure is performed using the medical instrument 51, it is not inserted into the channel of the endoscope. For this reason, the third region 63 is formed using the element wire whose diameter is greater than those of the first region 61 and the second region 62. In other words, the third region 63 has higher rigidity than the first region 61 and the second region 62.

Further, the insertion part 60 may be covered with a blade splicing the element wire and a tube formed of a resin material as needed.

The treatment part 70 has a well-known basket structure formed of a plurality of linear members 71, each of which is formed of metal. The plurality of linear members 71 are bundled by a tip 72 at the distal end side of the treatment part 70. The manipulation wire 73 is connected to the proximal end of the treatment part 70. The manipulation wire 73 passes through the insertion part 60 to extend up to the manipulation part 80.

The manipulation part 80 includes a tubular main body 81, a manipulation rod 82, and a handle 83. The manipulation rod 82 is attached to the proximal end of the manipulation wire 73. The manipulation rod 82 includes a rack 82A and a knob 82B. The handle 83 is connected to an engaged gear 83A with a rack 82A in the main body 81. When an operator grasps the knob 82B to retreat the manipulation wire 73 relative to the main body 81, the linear members 71 of the treatment part 70 can be housed in the insertion part 60, as enlarged and shown in FIG. 14. However, since a maximum outer diameter of the tip 72 is greater than an inner diameter of the insertion part 60, the tip 72 cannot completely go into the insertion part 60.

An operation of the above-mentioned medical instrument 51 according to the present embodiment when in use will be described taking a procedure of removing a calculus from a bile duct by way of example.

An operator introduces a distal end of a side-viewing endoscope up to the vicinity of the duodenal papilla of a patient. The operator inserts the medical instrument 51 from a forceps port with the treatment part 70 housed in the insertion part 60. The operator advances a distal end of the medical instrument 51 up to the vicinity of a distal end of the channel of the endoscope.

The operator observes the vicinity of the duodenal papilla using the endoscope. Simultaneously, the operator manipulates an elevator installed on the distal end of the endoscope to bend the distal end of the medical instrument 51 so that the distal end of the insertion part 60 is directed to the duodenal papilla. The operator inserts the medical instrument 51 from the duodenal papilla into the bile duct.

The operator checks a position of the treatment part 70 using, for example, an X-ray fluoroscopic image. Simultaneously, the operator advances the medical instrument 51 up to a position of the calculus. Here, the compressive force is barely applied to the insertion part 60. For this reason, the insertion part 60 sufficiently exerts flexibility to follow a shape of the bile duct.

When the treatment part 70 arrives near the calculus, the operator manipulates the knob 82B to advance the manipulation wire 73 relative to the insertion part 60, thereby causing the treatment part 70 to protrude from the insertion part 60. The operator entraps the calculus in an internal space of the basket made up of the metal element wire, and retreats the manipulation wire 73. Then, the calculus is captured in the treatment part 70.

When the calculus captured in the treatment part 70 is larger than an opening diameter of the duodenal papilla, the operator manipulates the handle 83 to retreat the manipulation wire 73 with great force. Thereby, the calculus is crushed. Here, the insertion part 60 is sandwiched between the calculus and the manipulation part 80. For this reason, a great compressive force is applied to the insertion part 60 in the axial direction.

However, the first and second regions 61 and 62 of the insertion part 60 maintain a predetermined curved state without assuming a linear shape even when the compressive force is applied. For this reason, the first region 61 follows the shape of the bile duct even with the element wires forming the neighboring loops in close contact to prevent buckling. Furthermore, the second region 62 follows the channel shape of the endoscope. As a result, an operator can perform a procedure without applying a great load to the bile duct. Furthermore, it is difficult to produce great friction between a channel wall of the endoscope and the insertion part 60. In this case, before the compressive force is applied, the first region 61 and the second region 62 are previously curved according to a surrounding shape. For this reason, when the compressive force is applied, the first region 61 and the second region 62 are curved in the same direction as a curved direction at the time.

It has already been described that, when the compressive force is applied, the curvature radius of the second region 62 is set so as to be greater than that of the first region 61. This is responsible for an environment of use in which, because a curve of the bile duct or a flexure caused by the elevator is stronger than a curve of the channel of the endoscope, the distal-end-side first region 61 is more curved.

When used to remove the calculus from the bile duct as mentioned above, the first region 61 may be configured, for example, so that a length thereof is set to about 100 to 250 mm, and so that a curvature radius thereof during the compression is set to about 50 to 300 mm, and preferably about 50 to 200 mm. The second region 62 may be configured so that a length thereof is set to about 1200 to 1800 mm, and so that a curvature radius thereof during the compression is set to about 300 to 3000 mm, and preferably about 500 to 1500 mm.

An example of element wire processing for manufacturing a coil realizing the curvature radius of the first region 61 is as follows.

Using the element wire which has a width of 0.58 mm, a thickness of 0.2 mm, a curvature radius of the convex part of 0.1 mm, a depth of the concave part of 0.026 mm, a curvature radius of the concave part of 0.12 mm and in which opposite thickness-directional lateral surfaces are parallel, a coil having the above-mentioned angle θ of 1.6° and an inner diameter of 2 mm is wound.

In the case of the finished coil, in the linear state, the top part of the convex part and the deepest part of the neighboring concave part are separated by 0.007 mm in the axial direction of the coil. In the radial direction of the coil, the side of the top part is 0.015 mm nearer the axis than the deepest part.

When the coil is compressed in the axial direction, a movable loop is generated. At one radial side of the movable loop, the top part and the deepest part are approximately in contact with each other. At the other radial side of the movable loop, due to movement, a distance between the top part and the deepest part is increased by 0.019 mm in the axial direction of the coil, and by 0.034 mm in the radial direction of the coil. As a result, an axial inclination of 0.5° occurs between the movable loop and the neighboring loop. As this inclination is accumulated, the coil has a curvature radius of 69 mm in a predetermined curved state when compressed.

Of course, in the medical instrument used for the other usage, each of the above-mentioned dimensions is not limited to this. The number of regions, lengths of the regions, and curvature radii of the regions during the compression may be appropriately set. The curvature radius of the distal-end-side region during the compression may be set so as to be greater than that of the proximal-end-side region during the compression.

Figure 14:
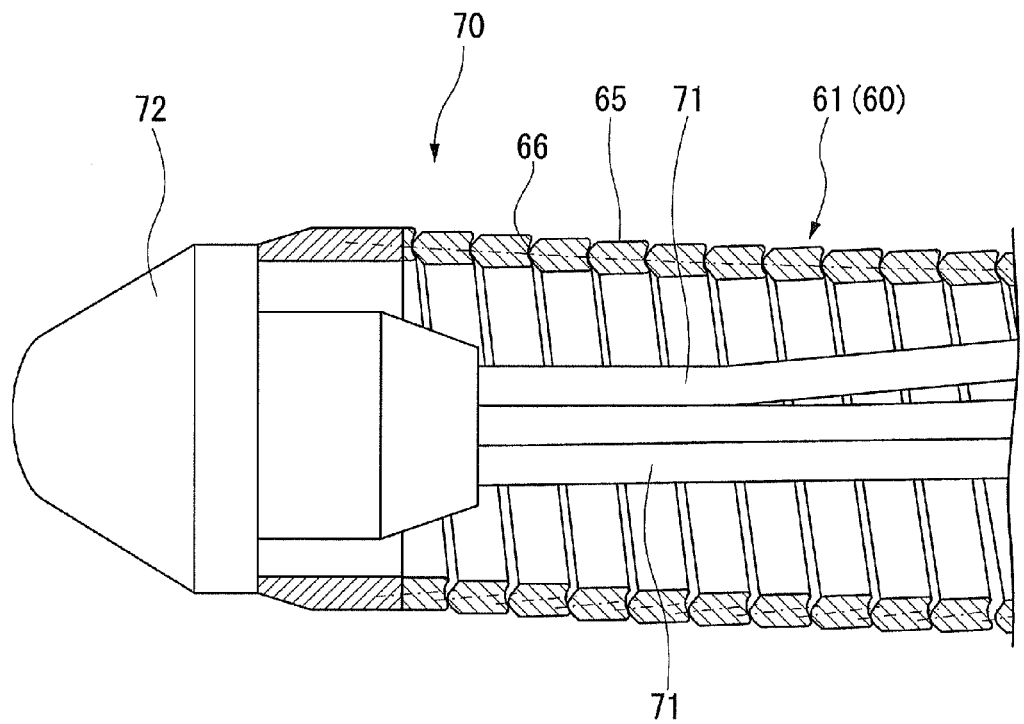
FIG. 14 is an enlarged cross-sectional view showing a proximal end of the medical instrument according to the third embodiment of the present invention.
Figure 15:
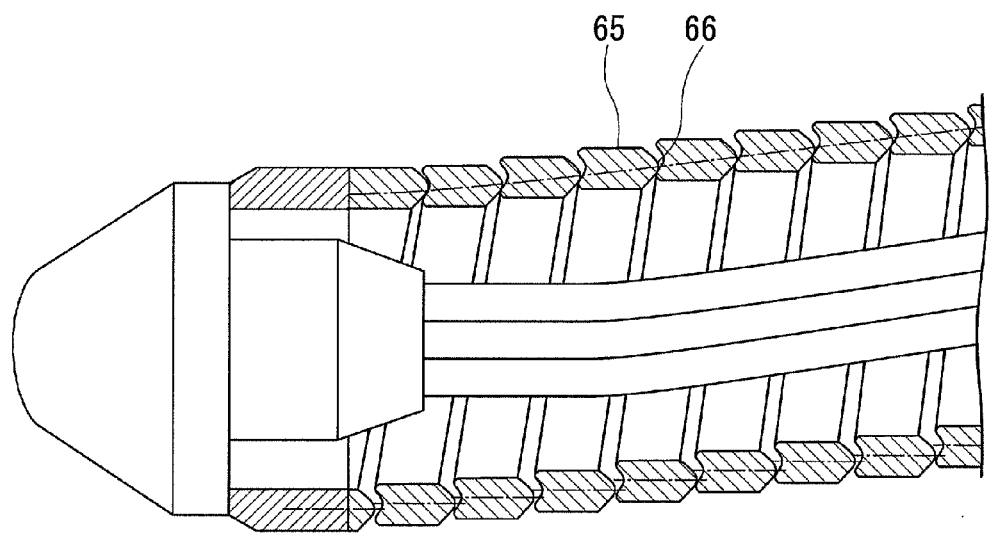
FIG. 15 is an enlarged cross-sectional view showing a proximal end in a modification of the medical instrument according to the third embodiment of the present invention.

In the present embodiment, as shown in FIG. 14, the example in which the convex part 66 is directed to the distal end side in the element wire 65 of the insertion part 60 has been described. Instead of this, as shown in FIG. 15, the insertion part may be configured so that the convex part 66 is directed to the proximal end side. Then, when the medical instrument is retreated relative to the endoscope, it is difficult for the channel or the elevator to get caught on the insertion part. For this reason, an operator can smoothly perform a retreat manipulation after the capture of the calculus. On the other hand, when the convex part is directed to the distal end side, there is a characteristic that it is difficult for the medical instrument to get caught when it is advanced. For this reason, how to configure the insertion part may be appropriately decided in consideration of the use of the medical instrument.

While each embodiment of the present invention has been described, the technical scope of the present invention is not limited to each embodiment described above. The present invention may be modified in various ways without departing from the spirit or teaching of the present invention.

For example, in each embodiment described above, the example in which, in the element wire, the top part and the deepest part are at only one point has been described. However, the top part and the deepest part may be at multiple places. The top part and the deepest part may be over a constant range in the thickness direction of the element wire.

Figure 16:
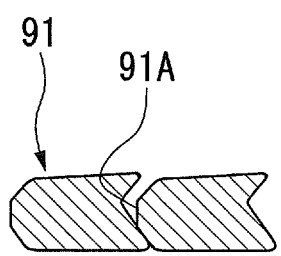
FIG. 16 is a cross-sectional view of a modification of an element wire that is a material of the medical coil according to each embodiment of the present invention.
Figure 17:
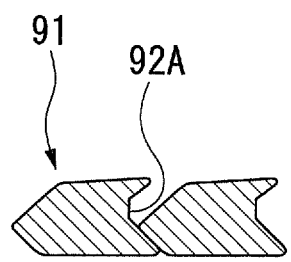
FIG. 17 is a cross-sectional view of a modification of an element wire that is a material of the medical coil according to each embodiment of the present invention.

A modification shown in FIG. 16 is an example in which a top part 91A of an element wire 91 is over a constant range in the thickness direction. A modification shown in FIG. 17 is an example in which a deepest part 92A of an element wire 92 is over a constant range in the thickness direction. In any case, when an axial compressive force is applied, any one point of the top part can slide on a surface of the concave part to approach the concave part. For this reason, a medical coil manufactured using the element wires 91 and 92 can produce effects similar to those of the above-mentioned medical coil.

To make it possible to slide to approach in this way, at least one of the convex part and the concave part may be formed so as to have a slant face.

In the medical instrument according to the present embodiment, the treatment part is not limited to one having the basket structure as described above. As the treatment part, a variety of well-known treatment parts may be used. When the treatment part is configured so that the compressive force is applied to the insertion part when the treatment part is operated, it is possible to obtain greater effects.

Even in the medical instrument having no treatment part, the medical coil according to the embodiment of the present invention may be approximately applied. For example, the medical coil according to the embodiment of the present invention may be applied to the insertion part such as a guide sheath used for insertion of, for example, a guide wire or a stent inserted into a relatively small diameter of lumen tissue such as a bile duct or a blood vessel. In this case, after the insertion part of the medical instrument is inserted into the lumen tissue, when there is a spot requiring great force for a breakthrough due to stenosis or calcification, the compressive force is applied to the insertion part by, for example, the manipulation wire. Thereby, buckling resistance of the insertion part can be enhanced in a form taken along the shape of the lumen tissue. As a result, the insertion part can break through the spot without placing a great burden on the lumen tissue.

The main points of the present invention are as follows.

A medical coil (1, 21) formed in a shape of a rod having an axis (X1, X2) by performing spiral winding on a band-like element wire (10, 30) is characterized in that:

when the medical coil is viewed from a cross section including the axis, a convex part (13, 33) is formed at one widthwise end of the element wire, and a concave part (14, 34) is formed at the other widthwise end of the element wire;

a straight line connecting a crest (top part 13A, 33A) of the convex part and a root (deepest part 14A, 34A) of the concave part is not parallel to the axis; and when the medical coil receives an external force along the axis, the crest of the convex part and the root of the concave part which are adjacent to each other approach each other.

A method of manufacturing the medical coil (1, 21) includes:

a process of forming the band-like element wire (10, 30) having the convex part (13, 33) and the concave part (14, 34); and a process of reeling out the element wire while pressing a lateral surface between the one end and the other end of the element wire so that an extension direction of the element wire forms an inclination with respect to a concave pressing surface (101) of a die (100), thereby forming the spiral winding.

The present invention is not limited by the description above, but it is limited by the scope of the appended claims.

DESCRIPTION OF REFERENCE NUMERALS

1, 21 medical coil
10, 30, 65, 91, 92 element wire
11, 12, 31, 32 lateral surfaces
13, 33, 66 convex part
13A, 33A, 91A top part
14, 34 concave part
14A, 34A, 92A deepest part
15A, 15B, 16A, 16B, 35A, 35B, 36A, 36B slant faces 51 medical instrument
60 insertion part
61 first region
62 second region
100 die
101 pressing surface
r1, r2 curvature radius
X1, X2 axis
θ angle

The invention claimed is:

1. A medical coil which is formed by winding an element wire, comprising:
 a plurality of loops formed by helically winding the element wire, the plurality of loops being disposed on a same axis,
 a convex part which is provided on a first end surface of each of the plurality of loops in an axial direction of the medical coil; and
 a concave part which is provided on a second end surface of each of the plurality of loops in the axial direction of the medical coil,
 wherein a line forming a connection between an upper most part of a top part of the convex part and a deepest part of the concave part forms a non-zero angle relative to a longitudinal axis of the medical coil in a natural state in which a compressive force is not applied in the axial direction, and
 the concave part has a slant face, and when the compressive force is applied in the axial direction of the medical coil, the top part of the convex part is configured to slide on the slant face of the concave part and to approach the deepest part.

2. A medical instrument having an insertion part which is longitudinal, in which at least a part of the insertion part is configured to include the medical coil according to claim 1.

3. The medical instrument according to claim 2, wherein:
 the insertion part has a first region configured to include a first medical coil and a second region configured to include a second medical coil; and
 the first region and the second region are different in a curvature radius of a curved shape when a compressive force is applied in the axial direction.

4. The medical coil according to claim 1, wherein
 the medical coil has a plurality of loops around the axis,
 a lateral surface of the element wire of each loops forms a predetermined angle with respect to the axis of the medical coil, and
 the top part and the deepest part are not in contact with each other in the natural state in which the compressive force is not applied in the axial direction.

5. The medical coil of claim 1, wherein
 the line forming a connection between an upper most part of a top part of the convex part and a deepest part of the concave part of a first loop of the plurality of loops is offset from the line of a second loop of the plurality of loops.

6. The medical coil of claim 1, wherein
 the convex part is continuously provided in a circumferential direction on the first end surface of each of the plurality of loops,
 the concave part is continuously provided in a circumferential direction on the second end surface of each of the plurality of loops,
 the convex part has a slant face, and
 the slant face of the convex part contacts the slant face of the concave part in the natural state.

* * * * *

UNITED STATES PATENT AND TRADEMARK OFFICE
CERTIFICATE OF CORRECTION

PATENT NO. : 9,089,264 B2  
APPLICATION NO. : 13/736360  
DATED : July 28, 2015  
INVENTOR(S) : Yoshihisa Kaneko et al.

Page 1 of 1

It is certified that error appears in the above-identified patent and that said Letters Patent is hereby corrected as shown below:

Please change Item (71) on the title page from "Applicant: OLYMPUS MEDICAL SYSTEMS CORP., Tokyo (JP)" to -- Applicant: OLYMPUS CORPORATION, Tokyo (JP) --.

Signed and Sealed this  
Seventeenth Day of May, 2016

Michelle K. Lee  
*Director of the United States Patent and Trademark Office*